United States Patent [19]

Hanna

[11] Patent Number: 4,815,463
[45] Date of Patent: Mar. 28, 1989

[54] SURGICAL APPARATUS FOR RADIAL KERATOTOMY

[75] Inventor: Khalil Hanna, Paris, France

[73] Assignee: Laboratoire Hydron, Neuilly S. Seine, France

[21] Appl. No.: 769,626

[22] PCT Filed: Dec. 20, 1984

[86] PCT No.: PCT/FR84/00298
§ 371 Date: Aug. 14, 1985
§ 102(e) Date: Aug. 14, 1985

[87] PCT Pub. No.: WO85/02763
PCT Pub. Date: Jul. 4, 1985

[30] Foreign Application Priority Data

Dec. 21, 1983 [FR] France ............... 83 20461

[51] Int. Cl.⁴ .......................................... A61B 17/32
[52] U.S. Cl. ........................................ 128/305; 128/751
[58] Field of Search .................. 128/305, 751, 755

[56] References Cited

U.S. PATENT DOCUMENTS

| | | | |
|---|---|---|---|
| 4,205,682 | 6/1980 | Crock | 128/305 |
| 4,246,895 | 1/1981 | Rehder | 128/305 |
| 4,340,059 | 7/1982 | Marinoff . | |
| 4,429,696 | 2/1984 | Hanna | 128/305 |

FOREIGN PATENT DOCUMENTS 2364646  4/1978  France .
2490954  4/1982  France .

Primary Examiner—William L. Freeh
Attorney, Agent, or Firm—Cushman, Darby & Cushman

[57] ABSTRACT

The present invention relates to apparatus for radial keratotomy. A support (1), having a reference surface (3) adapted to fit the cornea (2a) of an eye (2) and in which opens slits (19) disposed in planes including an axis (4) adapted to coincide with the optical axis (105), carries blades (22) of which each is associated with a respective slit (19), and means for simultaneously moving the assembly of blades (22) for a movement in the associated slits (19) towards or away from the axis (4); the blades (22), projecting with respect to the reference surface (3), then simultaneously cut the cornea (2a), advantageously pressed pneumatically against the reference surface (3). The simultaneous making of all the incisions is rapid, and the blades work in identical conditions so the incisions have reproducible geometric characteristics and the risks of perforation of the cornea are reduced.

36 Claims, 6 Drawing Sheets

FIG_1

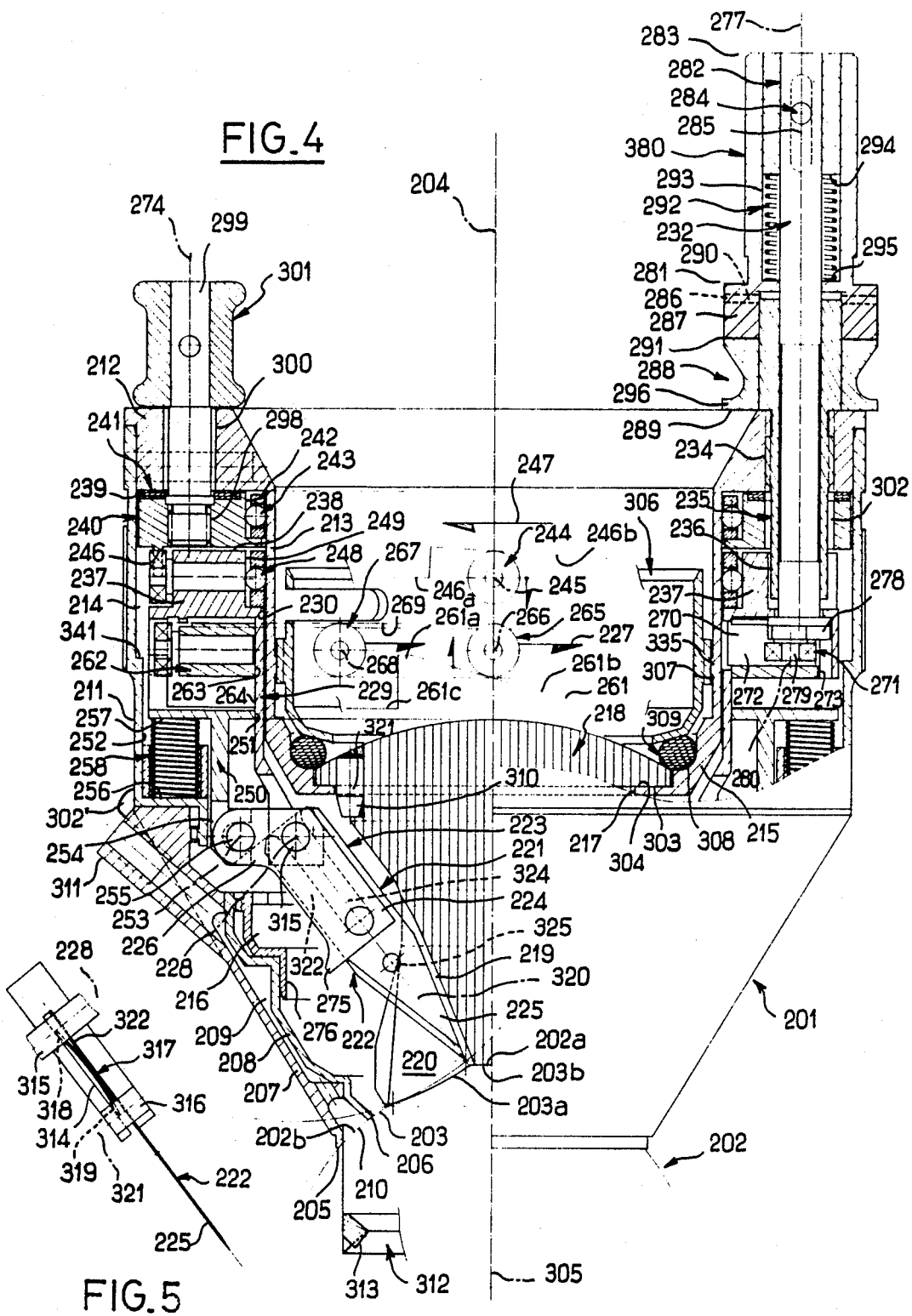

SURGICAL APPARATUS FOR RADIAL KERATOTOMY

The present invention relates to surgical apparatus for radial keratotomy.

By radial keratotomy is intended a surgical method consisting of modifying the curvature of the cornea of an eye by practising on this cornea radial incisions with reference to the optical axis of the eye. This radial keratotomy is particularly used for reducing the curvature of the cornea in a central zone or optical zone of it, either in a manner to adjust for correcting simple myopia, or, when there is simple astigmatism or associated with myopia, respectively in a localised manner corresponding to the most curved meridian of the astigmatism or in a modulated manner, by an appropriate choice of the number and position of the incisions, and of the depth, and of their respective ends towards and away from the optical axis.

For performing this radial keratotomy, various devices have been previously proposed which all use a single knife which the surgeon uses manually for successfully carrying out the different incisions and which differ only by the more or less sophisticated means of guiding of the knife for carrying out each of the successive incisions.

The most simple of these known devices is described in the review "Ophthalmology" of January 1983 (Volume 90-No. 1-PERK Study), and consists of a knife composed of a handle and a sharp blade passing through a guard acting as an abutment foot of the device on the cornea. The size of the projection formed by the blade with respect to the guard can be adjusted by micrometric displacement members, and determines the depths of the incisions; the incisions are made by a rolling turn of this knife, which is displaced the length of a mark previously made on the cornea, for example by means of a device of the type described in the French Certificate of Utility No. 2 490 954 or by the applicant of French Pat. No. 2 530 949, across a central zone and in the direction of the limbus.

The use of such a device leaves much to the manual dexterity of the surgeon, and is characterised by its lack of precision whatever this dexterity, if only because some of the incisions, for example 8 in number, are inconvenient to make since they are situated to the surgeon's left hand. In addition, the time necessary for making the different incisions is sufficient for the lamp of the operating microscope to cause a substantial dehydration of the cornea, with as a result a variation in the thickness of it, difficult to predict and in consequence to take into account progressively as the incisions are made. As a result there is a significant risk that the depth of incision made as a function of the thickness of the cornea in its normal state, transferred by the initial adjustment of the size of projection formed by the blade with respect to the guard, becomes excessive for the last incisions made, culminating in a perforation of the anterior chamber, greatly complicating the operation.

In addition, the making successfully of different incisions in the course of the operation causes loss of rigidity of the cornea, the ocular globe becoming hypotone, so that the last incisions are very difficult to make.

U.S. Pat. No. 4,340,059 describes a very similar device, except that in the place of applying on the eye by the means of a guard forming an abutment foot, the knife is applied on a curvilinear slide carried by a mechanical immobilisation pincer on the eye and intended to be placed in a plane including the optical axis such that the curvature of this slide is homothetic with the natural curvature of the corresponding zone of the cornea. A micrometric adjustment permits adjustment of the depth of incision but the limits of this latter respectively towards and away from the optical axis result from a simple visual control, by reference to a graduation carried by the slide. This device seems at first sight to offer a precision independent to a greater or lesser extent of the dexterity of the surgeon. However, the coercive guiding of the knife in the slide presenting a determined form and occupying a determined position with respect to the eye considered in the assembly does not permit a uniform depth of incision if one takes into account on the one hand that the cornea, before the incision, can have different forms which are not necessarily homothetic with the slide, and on the other hand the cornea is deformed to a greater or lesser extent by the incisions made as mentioned above. As a result, this device does not in reality bring about the solution of the inconveniences of the previously mentioned device.

For helping with the regularity of depth of incision as well as the form and position of the different incisions, it has been proposed to associate to a knife provided with a guard from which a sharp blade forms a projection, a template for guiding the blade and for abutment of the guard of the knife, which template presents a concave reference surface adapted to fit the cornea, a convex surface arranged a determined distance, possibly variable, from the reference surface for serving as an abutment to the guard of the knife, and a plurality of slots arranged in a star for permitting passage of the blade of the knife. The review "Ophthalmic Surgery" (Volume 12-No. 8-August 1981-pages 561 to 566-Kramer & Al) describes a template of this type, in which the slots open into a central space, whilst U.S. Pat. No. 4,406,285 describes a template of this type in which each slot has two ends, limiting respectively incision in the direction of an approach towards the optical axis and an extension away from this axis.

Such templates have the advantage of avoiding a direct abutment of the guard of the knife on the eye and of minimising the local effects developed on the cornea. In addition, such templates permit improving of the regularity of the depth of incision, determined by the value of the projection which the blade of the knife makes with respect to the reference surface, and possibly, by choice of a template of which the thickness is variable, of providing without difficulty a variation of the depth of incision, for example according to whether one approaches or extends away from the optical axis. However, the adjustment of the depth of incision can only be made by changing the template for a given knife, which means that a significant stock of templates must be kept. In addition, the length of each incision is imprecise if one cannot use, for determining it, the ends of the slots and, as a result of the fact that the incisions are made successively, on the one hand the operation occupies a long time with the inconveniences already noted above, and on the other hand the cornea progressively loses its rigidity as the incisions are made so that the last incisions are particularly difficult to make.

The object of the present invention is to propose a radial keratotomy apparatus remedying these inconveniences and, for this, the present invention proposes:

a support having an axis, a concave reference surface on the support secant to the axis thereof and adapted to fit the cornea of an eye in a position in which the axis of the support coincides with the optical axis of the eye, a plurality of slots in the support of which each is arranged with a respective plane including the axis of the support and opens into a zone of the reference surface, each slot permitting the passage of a blade of such a type that said blade has an active part forming a projection determined with respect to the reference surface and can move in the plane of the slot between two dertermined limits, respectively of approach and extension of the active part of the blade with respect to the axis of the support, and characterised in that the support has a plurality of blades of which each is associated with a respective slot and means arranged behind the reference surface for bringing about simultaneous displacement of the blades with respect to the support, in the respective associated slots and in their respective planes, from a first of the two said respective determined limits to the second of these two respective determined limits and at the said respective determined projection of an active part of each blade.

Thus, all the incisions are made simultaneously, so that at each instant of the operation, the active part of the different blades encounter an identical mechanical resistance on the cornea, and that the mechanical conditions of the incisions are the same for all incisions. In addition, the duration of the operation necessary to make all the incisions wanted is considerably reduced, which is advantageous in itself and eliminates in addition all risk of dehydration of the cornea under the lamp of the operating microscope and thus its consequences.

There results a great geometric precision of the incisions, whatever it should be added the position of these latter with respect to the hand of the surgeon, and a considerable reduction of all the risks, particularly of perforation, resulting from the progressive variation of thickness of the cornea, by dehydration, and the consistency of the cornea, by progressive weakening, which is encountered in the known techniques for making successive incisions.

Preferably, the said first and second limits are respectively the limit of approach and limit of extension of the active part of each blade with respect to the axis of the support, which signifies that the active parts of the blades making the different incisions in extending from the optical axis work in tension with respect to the central zone of the cornea. While one can equally carry out the incisions via a reverse displacement of the active parts of the blades, particularly when, in accordance with a preferred embodiment of the apparatus, this latter has means for pneumatically pressing the cornea against the reference surface, which on the one hand overcomes any risk of wrong incision due to possible asphericity and elasticity of the cornea, and on the other hand ensuring maintained efficacy of the apparatus and of the cornea in relative position. For this, advantageously, the support delimits in a fluid tight manner, about the blades, a volume open only towards the reference surface particularly via the said slots and having means for connection of the said volume to a source of vacuum, which permits neutralisation of the resistance of the cornea to the penetration of the blades and ensures a reproducability of the depth of the incision.

The relative desired position of the apparatus and of the cornea can be obtained more easily, by successive approximations, previous to the making of the incisions, when the apparatus according to the invention has in addition means for permitting withdrawal in a reversible manner, for this, of the active part of the blade with respect to the reference surface. The visibility through the apparatus, to the operating microscope, particularly during positioning of the apparatus on the cornea previous to the making of the incisions can be substantially helped when, according to a preferred embodiment, the reference surface has a lens forming an integral part of the support and having the said slots. Naturally, this lens facilitates the centering in view of the fact that it has advantageously marking means, such as a central reticule and a circle of predetermined diameter, and the surveillance of the good making of incisions.

Such apparatus according to the invention can be used for making incisions with different geometric characteristics when, as is preferred, means are provided for adjusting the projection of the active part of the blades with respect to the reference surface, which permits adjusting of the depth of the incisions, as well as for adjusting the position, spacedly with respect to the axis of the support, of the first and the second limits mentioned, that is to say the position of each active part of the blades with respect to the axis of the support respectively at the beginning and end of incision. It should be noted that the path of the active parts of the blades as well as the geometry of the reference surface, advantageously interchangeable at least as to its zone in which the slot open, can be chosen so that the depth of the incision is constant or varies in a predetermined manner as a function of the separation from the axis of the support, with which coincides the axis of the support. Particularly, the reference surface can have a limited convexity in an annular zone situated around the axis of the support and into which the slots open, the presence of the pneumatic means for pressing the cornea against the reference surface permitting fitting without difficulty of this convexity to the cornea, of which the normal convex curvature is thus locally reversed.

In fact, the blades are advantageously removable and interchangeable, which permits particularly use of blades regularly angularly spaced about the axis of the support, and thus correcting myopia, or to use blades localised in determined angular sectors, with reference to the axis of the support, for correcting an astigmatism. In one or other case, the geometric characteristics of the incisions made by the different blades can be adjusted thanks to the different means of adjustment mentioned, or by the association in different slots of a blade presenting themselves the different geometric characteristics and by the choice of a reference surface with appropriate geometry in its zone in which the slots open.

These possibilities are offered together by a single apparatus, easy to use, and permitting practising of incisions in these reproducable conditions, that is to say offering a better predictability of result with different surgeons.

Other characteristics and advantages of the apparatus according to the invention will appear from the following description, relating to two non-limitative embodiments, as well as the accompanying drawings which form an integral part of this description.

FIG. 4 shows a second embodiment of the apparatus according to the invention, partly in side elevation and partly in cross-section on a plane including the axis of the support.

FIG. 5 illustrates a detail of the mounting of a blade of the apparatus of FIG. 4, in a cross-sectional view on a plane represented by V—V in this figure.

Figure 1:
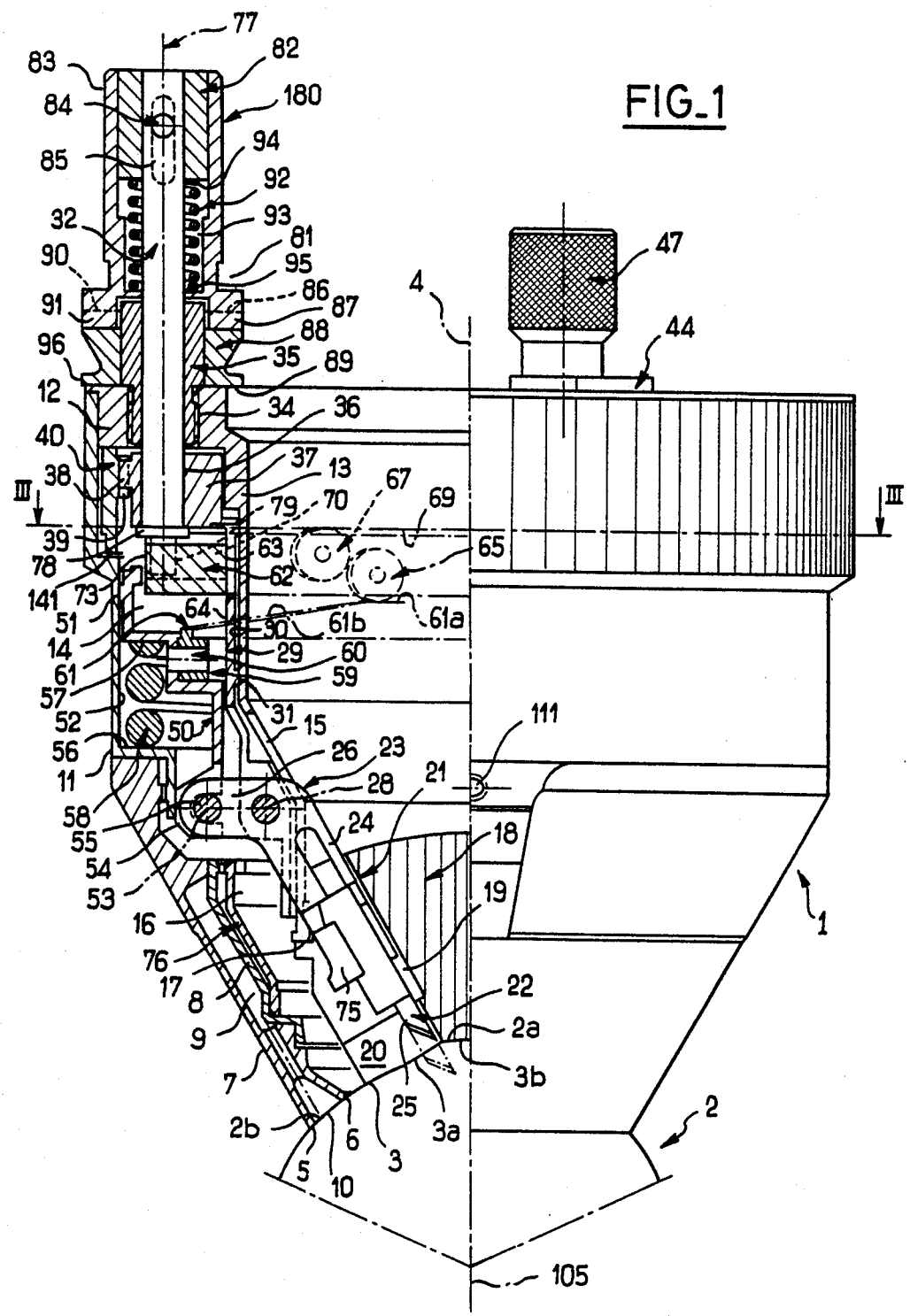
FIG. 1 shows a first embodiment of an apparatus according to the invention, half in side elevation and half in cross-section on a plane including the axis of the support, and shown as I—I in FIG. 2.

It should be noted that FIGS. 1 and 4 show the apparatus in a position close to its normal use position on an eye of a lying-down patient. Any intimation of relative orientation or level appearing in the following description will be understood by reference to this normal use position such as is illustrated in FIGS. 1 and 4.

In the first instance, FIGS. 1 to 3 will be described, and more particularly FIG. 1 where the apparatus according to the invention is seen to have a body 1, forming a support, by which the apparatus can be held and manipulated, and can be placed on the cornea 2a of an eye 2 via a concave reference surface 3 adapted to fit this cornea 2a as well as the juxta-limbic sclere 2b in a position in which an axis 4 of the support 1 coincides with the optimal axis 105 of the eye. In the illustrated example, the reference surface 3, turned downwards in the use position of the apparatus, presents the general form of a portion of a sphere centred on the axis 4 and cutting it, with the exception of a convex, annular localised zone 3a, which will be described further. Nevertheless, other forms of the reference surface 3 can be adopted without departing from the scope of the present invention.

In a radially exterior peripheral zone, with reference to the axis 4, the reference surface 3 is defined by the respective edges 5,6, both annular about the axis 4, of two annular coaxial walls, respectively 7 and 8, respectively radially outer and radially inner. These walls 7 and 8 delimit between themselves, in a fluid tight manner, a volume 9 presenting in the reference surface 3, between the edges 5 and 6, a continuous, annular opening 10. The volume 9 can be connected, by an appropriate connection 111 in the wall 7, to a source of vacuum not shown, which permits provision at the opening 10 of the volume 9 of an atmospheric depression ensuring pressing of the juxta-limbic sclere 2b against the surface reference surface 3, so that the cornea 2a thus fits in the best way.

The two walls 7 and 8 are constituted by two distinct pieces, of generally trunco-conical form and tapering from top to bottom.

Upwards, the piece defining the wall 7 is connected in a fluid tight manner, fixed but removable, and for example by screwing, to a piece itself defining a wall 11 of a form generally circularly cylindrical about the axis 4; this piece is itself connected upwards, in a fluid tight manner, fixed and removable for example by an annular tight fit, to a wall 12, about the axis 4 and situated radially inside the wall 11, of a piece having in addition a wall 13 of a form generally circularly cylindrical with a maximum diameter less than the minimum diameter of the wall 11. Thus the wall 13 is positioned coaxially inside this wall 11 and the walls 11 and 13 delimit between themselves a volume 14 closed upwards by the wall 12, to which the wall 13 is connected upwards. Downwards, at a level above the connection of the walls 11 and 7, the wall 13 is connected to a wall 15 which is formed in one piece with this wall 13 as well as the wall 12 and which has a trunco-conical form and converges from top to bottom, leaving between it and the walls 7 and 8 a volume 16. The wall 15 is interrupted downwards by an annular edge 17 at a level above that of the edge 6 of the wall 8, and situated at a level above that of the edge 5 of the wall 7 taking into account the generally concave form of the reference surface 3, above which the edge 17 is situated when the edges 5 and 6 participate in the definition of this surface.

The wall 15 carries in a fixed manner, but preferably removable thanks to means not shown but easily conceivable by the man skilled in the art, a lens 18 circularly symmetrical about the axis 4 and which defines the zones of the reference surface 3 which zones are situated radially inwards, with respect to the edge 6 of the wall 8 which is situated radially inwardly, with respect to the edge 5 of the wall 7. Particularly, the lens 18 defines the annular zone 3a of the reference surface 3 advantageously provided with a reference circle for the axis 4, as well as a central zone 3b of the latter, the central zone 3b cutting the axis and having advantageously a centering reticule at its intersection with this axis 4. It should be noted that the lens 18 is totally cleared or unobstructed, upwards, by the assembly of the walls 15, 13, 12, 11, 8, 7 so that it is possible to see through the apparatus along the axis 4 as far as the edge 6 of the wall 8.

In the zone 3a of the reference surface 3 open several slots such as 19, arranged in the lens 18 and in the wall 15 in planes such as 20 of which each includes the axis 4 of the support. In the example illustrated, these planes such as 20, and with them the slots 19, are regularly angularly spaced about the axis 4 and are eight in number, but other relative dispositions and other numbers can equally be chosen without departing from the scope of the present invention.

Each of the slots 19 is able to receive, with the possibility of relative movement in its plane 20, a respective knife 21 formed with a blade 22 directed downwards, and a blade-carrier 23 in the form of an L, having two mutually fixed arms of which one, 24, is directed downwards, and is hollow for receiving in a fixed but removable manner, for example by resilient encasing and pinching, an upper end zone of the blade 22 having in addition projecting below this arm 24 a lower end zone or active zone 25, i.e. a cutting edge and an arm 26 to which the arm 24 approximately radially with reference to the axis 4. The two arms 24 and 26 as well as the blade 22 are arranged in the same median plane 20 as the slot 19 with which they are associated. It should be noted that with each slot 19 is associated a blade-carrier 23 to which can be associated a respective blade 22, it being noted that, in use of the apparatus, certain blade-carriers 23 can remain non-provided with blades, so that the apparatus can be used with a single blade, or with a number of blades corresponding to the number of slots, that is to say eight in the non-limitative illustrated example, or again with any intermediate number of blades in positions chosen at will amongst the positions of the different planes 20.

Essentially, each blade-carrier 23 is placed inside the volume 16 and is pivoted inside this volume, at the junction of its two arms 24 and 26, about a pin having an axis 28 perpendicular to the plane 20 of the associated slot 19, on a fork of an annular carrier 29 having the general form of a circularly cylindrical sleeve. The pivot axes 28 of the different blade-carriers 23 on this carrier 29 are placed in the same plane perpendicular to the axis 4 and tangent, at their point of intersection with the respective plane 20, to the same virtual circle 27 (FIG. 2) about the axis 4 in the illustrated example, but other relative dispositions of these axes and other forms of carrier 29 can be adopted without departing from the scope of the present invention.

The carrier 29 externally surrounds the wall 13 on which it is relatively slidingly mounted, in a manner to be able to accomplish with respect to it, that is to say with respect to the support 1, a tranlational or linear movement parallel to the axis 4 without being able to accomplish a movement in rotation about this axis 4 with respect to the wall 13 and to the support 1.

To this effect, for example, the wall 13 receives the carrier 29 via a face 30, radially outwards with reference to the axis 4 and circularly cylindrical, and the carrier 29 is in contact with this face 30 by annular bearings 31, radially inside with reference to the axis 4 and circularly cylinderical with a diameter substantially the same as that of the face 30. Rotation of the carrier 29 with respect to the wall 13 about the axis 4 is prevented by keying, by means of a rod 32 which extends parallel to the axis 4, with the possibility of relative sliding parallel to this axis, through the wall 12 via a bore 34 in the latter. The bore 34 is provided internally with a guide sleeve 35 for the rod 32 for sliding parallel to the axis 4, which rod 32 is engaged, via a bore 36 parallel to the axis 4, in an annular flange 37 that the carrier 29 presents integrally upwards and radially outwards, inside the volume 14.

Radially outwards the flange 37 of the carrier 29 has a screw thread 38 engaged with a complementary thread 39 which has, radially inwards an annular crown 40 housed inside the volume 14 with the possibility of rotation about the axis 4 with respect to the support 1, but without possibility of translational or linear movement with respect to this support 1 parallel to the axis 4. For example, for this, the crown 40 is abutted upwards against the wall 12 and downwards against a plane annular; shoulder 141 which the wall 11 presents inside the volume 14. The guiding of this crown 40 in rotation about vis-a-vis the support 1 is advantageously ensured by the intermediary of the carrier 29 from the fact of the mutual engagement of the screw thread 38 of the latter and the thread 39 of the crown 40.

In regard to the crown 40, the wall 11 is pierced by an arcuate aperture 41 situated in a median plane perpendicular to the axis 4, and in which is engaged a finger 42 carried in a fixed manner by the crown 40 for constituting a means of manual drive and manoeuvre of the crown 40 in rotation about with respect to the support 1. The carrier 29 which is immobilised in rotation with respect to the support 1, then submits from such crown rotation a translation, i.e. axial movements, parallel to the axis 4 with respect to this support, in a direction function of the direction of rotation of the finger 42 about the axis 4 and with an amplitude function of the amplitude of this rotation.

In the measurement where each blade-carrier 23, and with it the possibly associated blade 22, is displaced in such a translation conjointly with the carrier 29, one can thus bring about, by an appropriate rotation of the crown 40 by manoeuvring the finger 42, that the active zones 25 of the different blades 22 engaged in the blade-carriers 23 are in a withdrawn or retracted position, illustrated in full lines in FIG. 1, in which each active zone 25 of the blade 22 is placed withdrawn with respect to the reference surface 3, in the corresponding slot 19, or equally in a position, illustrated in broken lines in FIG. 1, in which the active zone 25 of each blade 22 forms a projection with respect to the reference surface 3 in the zone 3a of the latter, the size of this projection being a function of the angular position of the finger 42 with respect to the support 1, with reference to the axis 4.

For permitting visualisation, via the position of the finger 42 with respect to the body 1, the withdrawal of the active zones 25 of the blades 22 with respect to the reference surface 3, or the possible projection formed by these active zones 25 with respect to this reference surface 3 thus the size or extent of this possible projection, the wall 12 of the support 1 has externally, in the region of the arcuate aperture 41, a graduation scale 43 representative of the position of the active zones 25 of the blades 22 with respect to the surface 3 and, when there is a projection of the active zones of the blades 22 with respect to this reference surface 3, of the size of this projection which itself determines the depth of incision.

Further, means are provided for limiting this depth of incision, that is to say the size of the projection possibly formed by the active parts 25 of the blades 22 with respect to the reference surface 3, in the form of a slide 44 carried on top of the wall 12, by the intermediary of an arcutes slot 45 in this arranged in this in the proximity of the aperture 41. This slide 44 has an edge 46 adapted to form an abutment for the finger 42 when a rotation of the latter, with respect to the support 1, in a direction corresponding to the descent of the carrier 29, that is to say to the formation of a projection with respect to the active zones 25 of the blades 22 with respect to the reference surface 3. The slide has a manoeuvring button 47 threadedly engaged with a bolt extending up through the slot 45 and the slide 44. Removable locking of this slide 44 on the support 1 in a desired position along the length of the slot 45 can be had by by tightening the button 47.

The limitation of movement of translaton, i.e., axial movement, of the carrier 29 with respect to the support 1 in the direction of withdrawal of the active zones 25 of the blades 22 can be assured either by abutment of the flange 37 of the carrier 29 upwards against the wall 12, or by abutment of the finger 42 against one 48 of the ends 48,49 of the aperture 41.

By way of non-limitative example, one can thus provide the possibility of translation or axial movement of the carrier 29 with respect to the support 1, between two limits corresponding respectively to a withdrawal of the active parts 25 of the blades 22 supposedly standardised, with respect to the reference surface 3, by a distance of a tenth of a millimeter and a projection of this active part 25 with respect to the reference surface 3 of a distance of nine tenths of a millimeter, these limits being marked by numerical indications of the graduation scale 43 carrying also an indication of the projection corresponding to the intermediage positions between these limits.

In order that each position of the carrier 29 with respect to the support 1, in translation parallel to the axis 4, constitutes a stable position, the engagement of the screw thread 38 and the thead 39 assures an irreversible transmission of movement.

The mode of displacement of the carrier 29 with respect to the support 1 which will be described, supposing a translation without rotation of the carrier 29 with respect to the support 1, suits in the normal case, where, as is illustrated, the active zone 25 of each blade 22 is situated in a plane which coincides with the plane 20 of the associated slot 19.

Meanwhile one can equally provide that the active zone 25 of each blade 22 is situated in a plane which forms a determined angle, identical from one blade to the next, with respect to the plane 20 of the associated slot 19. In this case, the fixing of the flange 37 of the carrier 29 against any rotation about the axis 4 by means of the rod 32 traversing without play the sleeve 35 and the bore 36 of the flange 37, is done away with and replaced by a mutual connection between the carrier 29 and the support 1, and more precisely the wall 13 of the latter. The connection may be in the form of a helicoidal cam surface centered on the axis 4 of the support 1 and having an angle of helix compatible with the angle which forms the plane of each active zone 25 of the blade 22 with respect to the plane 20 of the associated slot 19, so that the translation of the carrier 29 with respect to the support 1 parallel to the axis 4, by manoeuvring of the finger 42, is accompanied by a rotation of the carrier 29 about the axis 4 with an amplitude such that the plane of the active zone of each blade remains fixed with respect to the support. The man skilled in the art can easily provide an apparatus according to the invention with such a conception, which is not illustrated, by providing a possibility for angular movement of the rod 32 with respect to the support 1, about the axis 4, the guiding without play of the rod 32 in a bore 36 of the flange 37 of the carrier 29 being preserved by reason of the functions of the rod 32 which will appear below. Further, one can in this case arrange to taper slots 19 in the region of the reference surface 3.

Further with respect to the means permitting displacement of the carrier 29, and with it the blades 22, for translation parallel to the axis 4 with respect to the support 1, the apparatus according to the invention has means for manoeuvring at will the assembly of blade-carriers 23 to pviot with respect to the carrier 29, about the respective axes 28, in the planes 20 of the respective associated slots 19.

Figure 2:
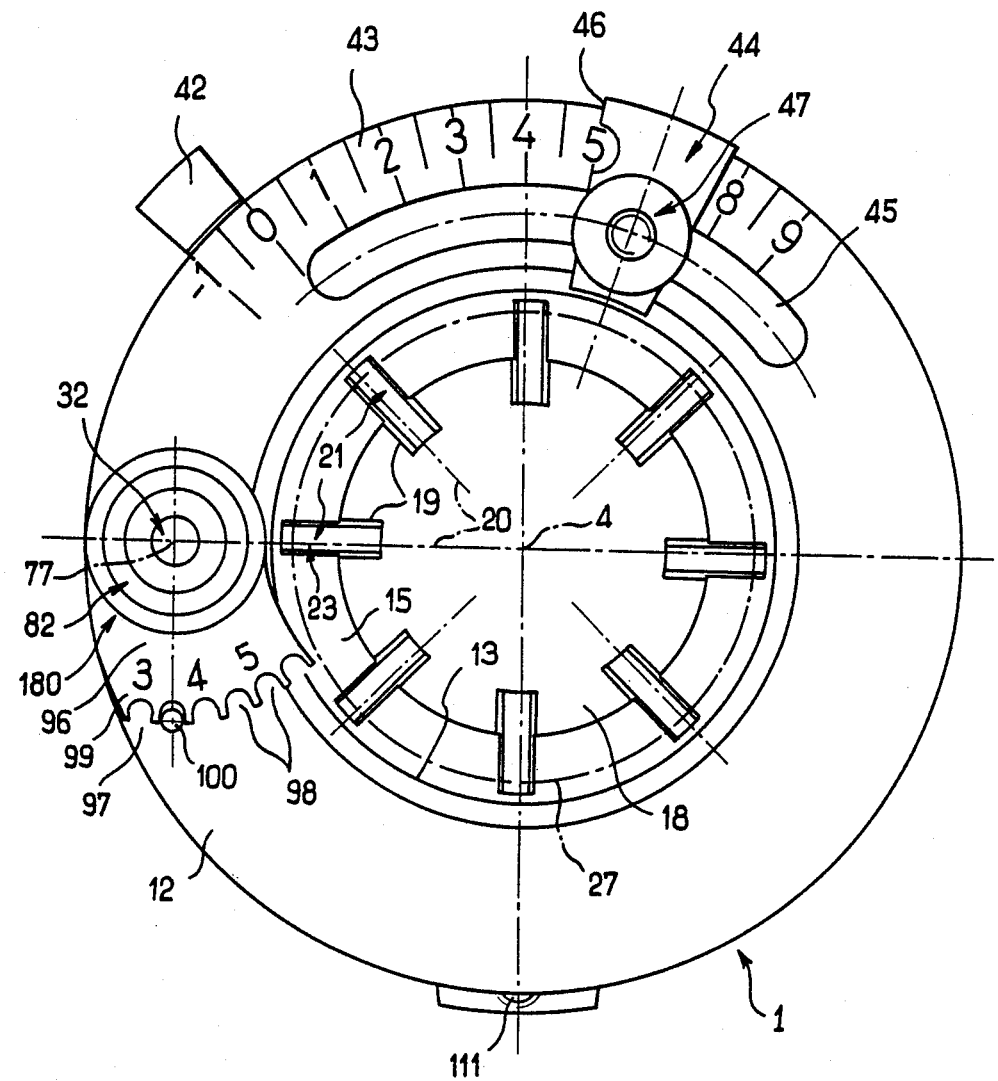
FIG. 2 shows in a plan view the apparatus illustrated in FIG. 1, that is to say a view in the direction of the axis of the support.
Figure 3:
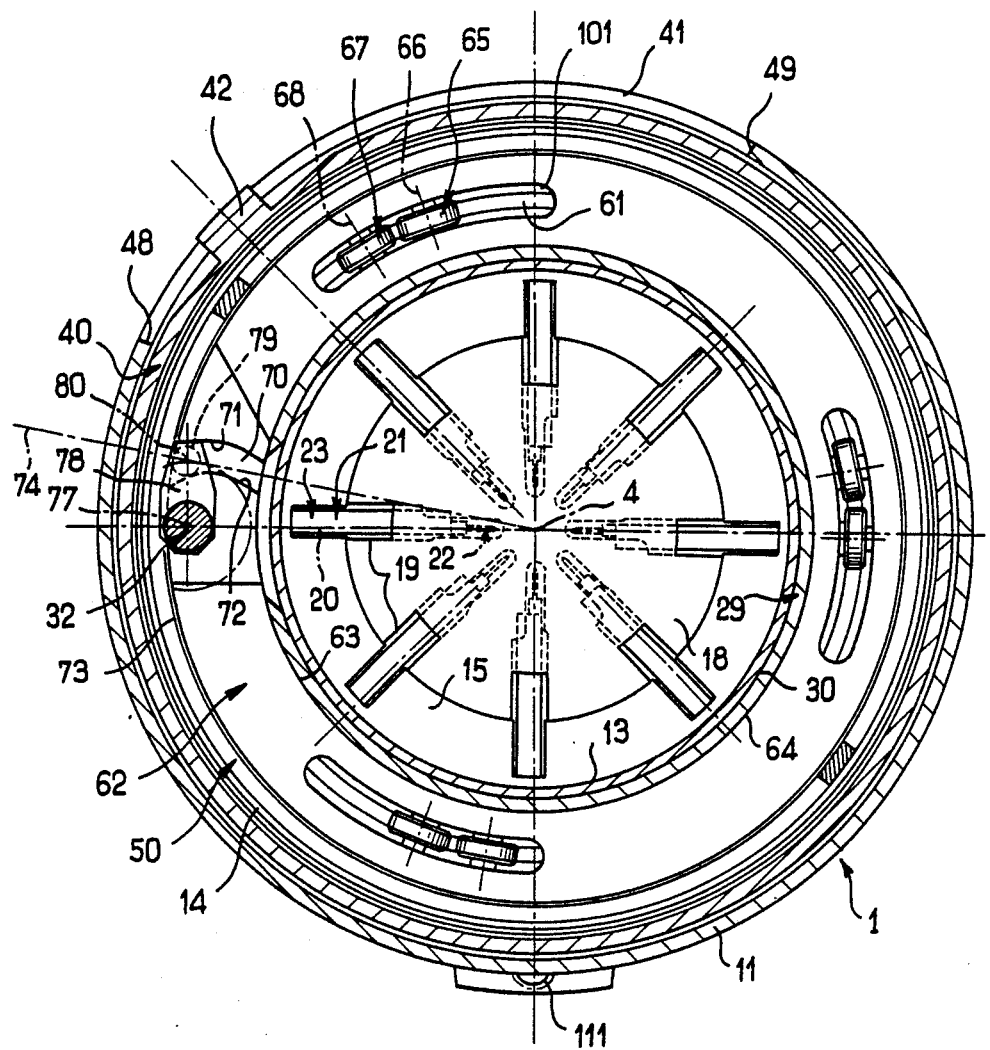
FIG. 3 shows a view of the apparatus in section on a plane perpendicular to the axis of support, shown as III—III in FIG. 1.
Figure 6:
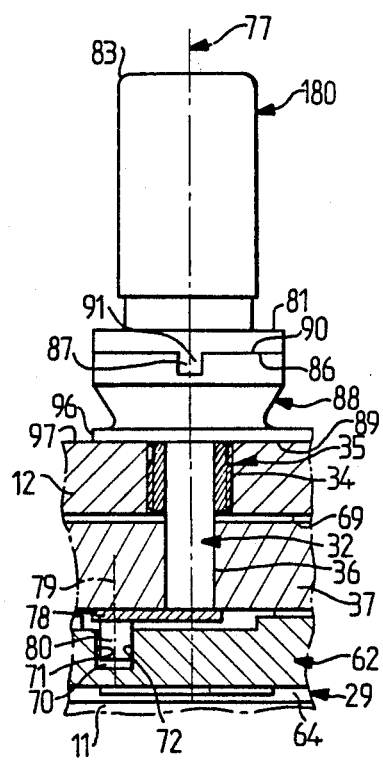
FIG. 6 is a fragmentary sectional view taken on line VI—VI in FIG. 1.
Figure 8:
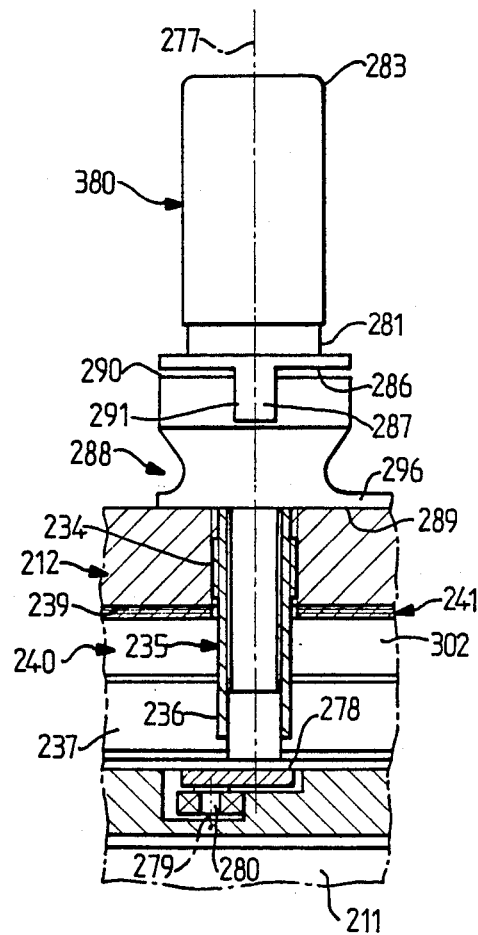
FIG. 8 is a fragmentary sectional view taken on line VIII—VIII in FIG. 4.
Figure 7:
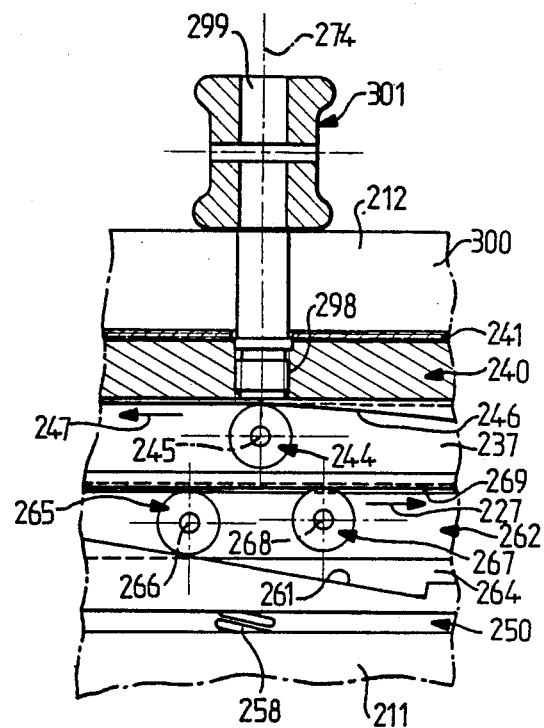
FIG. 7 is a fragmentary sectional view taken on line VII—VII in FIG. 4.

For this, the apparatus illustrated in FIGS. 1 to 3 has, inside the volumes 14 and 16, an annular sleeve 50 arranged coaxially with the carrier 29, radially outside this with reference to the axis 4, means being provided for guiding this sleeve 50 in translation or axial movement with respect to the carrier 29 parallel to the axis 4 without possibility of relative rotation about this axis.

For example, the guiding of the sleeve 50 in translation with respect to the carrier 29 parallel to the axis 4 is assured by contact of annular bearings such as 51 which are circularly cylindrical about the axis 4 and situated radially outside the sleeve 50, and on one face 52, radially inside with reference to the axis 4, which the wall 11 presents in view of the sliding of these annular bearings such as 51. The immobilisation of the sleeve 50 to rotation with respect to the carrier 29 about the axis 4 is assured, in the embodiment of the apparatus which is illustrated in FIGS. 1 to 3, by a connection of the sleeve 50, downwards, with each of the blade-carriers 23 by the intermediary of kinematic connection means associating, to a translation of the sleeve 50 with respect to the carrier 29 in one or the other of two opposite directions parallel to the axis 4, a simultaneous pivoting of the assembly of blade-carriers 23 with respect to the carrier 29, about the axes 28, so that the active zones 25 of the blades 22 are displaced radially respectively towards or away from the axis 4 of the support 1, in the planes 20 of the associated slots 19.

In the example illustrated in FIGS. 1 to 3, the means of kinematic connection are constituted on each blade-carrier 23 by a respective pivot pin 55 fixed to the arm 26 of the blade-carrier 23 in a zone further from the axis 4 than the pivot axis 28 of this blade-carrier 23 on the carrier 29. This pivot pin 55 has an axis 53 parallel to the axis 28 on the sleeve 50, these kinematic connection means comprise, for each blade-carrier 23, a lower stirrup part 54 open towards the axis 4 and adapted to engage in the pivot pin 55, without play, respectively above and below whilst there remains vis-a-vis the pivot pin 55 radial play, with reference to the axis 4.

It may be imagined that, by the lever effect, a translation of the sleeve 50 parallel to the axis 4 with respect to the carrier 29 provokes a pivoting of the blade-carriers 23 and the blades 22, in unison, with respect to the carrier 29 about the axes 28.

For bringing about at will of such a pivoting, the apparatus illustrated in FIGS. 1 to 3 has means for manoeuvring at will the sleeve 50 to translate with respect to the carrier 29 in one direction or the other, parallel to the axis 4.

For this, the wall 11 has a lower, plane shoulder 56, annular shoulder 56, which is directed upwards and the sleeve 50 has, opposite this shoulder 56, a plane annular shoulder 57, also centred on the axis 4 but facing downwards. Between these shoulders 56 and 57 is sandwiched a helicoidal compression spring 58 axis 4, resiliently urging the sleeve 50 to translate upwards, with respect to the carrier 29, parallel to the axis 4.

In addition are provided means for reversible manoeuvre, at will, of the sleeve 50 to translate with respect to the sleeve 29 parallel to the axis 4 in a direction opposed to the direction of action of the spring 58.

On the sleeve 50, these reversible manoeuvring means comprise an annular piece 59 fixed to the sleeve 50 by any appropriate means, by for example pins such as 60. Upwards, this piece 59 defines at least one accurate cam way fixed to the sleeve 50 and sloping with respect to the axis 4 more precisely in the illustrated example, the annular piece 59 has an upper annular face 61 with generatrices perpendicular to the axis 4, this face 61 having three identical plane sections 61a coplanar and perpendicular to the axis 4, with which alternate three identical sections 61b, regularly spaced about the axis 4, of which each presents a helicoidal form sunken with respect to the plane sections 61a.

On the carrier 29, these reversible maneuvering means comprise a collar 62, centered on the axis 4 and in sliding contact, by a circularly cylindrical face 63 centred on the axis 4 and radially inside with respect to this axis, with a face 64, also circularly cylindrical about the axis 4 with a diameter identical to that of the face 63, which the carrier 29 presents in the direction of radial extension with respect to the axis 4, so that the collar 62 is guided in rotation about the axis 4 with respect to the sleeve 29. Downwardly, with respect to the upper face 61 of the piece 59 and more precisely opposite each of the zones 61b of this face, the collar 62 carries a cam follower in the form of a respective disc 65 mounted for rotation in a slot about an axis 66 radial with respect to the axis 4. Upwardly, the collar 62 carries a plurality of discs 67 pivoting in the slots about respective axes 68 radial with respect to the axis 4. The collar 62 is held in application upwards, via these discs 67, on the plane, annular about the axis 4 and perpendicular to the latter, face 69, which the flange 37 of the carrier 29 presents downwards. In urging the sleeve 50 upwards with respect to the carrier 29, parallel to the axis 4, the spring 58 ensures permanent contact of the face 61 of the piece 59 with the discs 65 and with the discs 67 of the collar 62 with the face 69 of the flange 37 so that, by reason of the form of this face 69, the collar 62 is immobilised against translation with respect to the carrier 29, parallel to the axis 4.

The helix angle of the zones 61b of the face 61 of the piece 59 and the tendency of the discs 65 and 67 to rotate about their respective axes are chosen such that the action of the spring 58 alone returns, if it is not counterbalanced, the sleeve 50 into an upper limit position with respect to the carrier 29, by relative translation parallel to the axis 4, and provides for a rotation of the collar 62 from the application of the discs 65 against the sloping parts 61b of the face 61 of the piece 59. This high limit position corresponds to a position not illustrated in which each of the discs 65 is in contact with a lower zone of the associated part 61b of the face 61 of the piece 59, and in which the active zone 25 of each of the blades 22 occupies its furthest possible radially extended position with respect to the axis 4, taking account of the kinematic connection between the sleeve 50 and each of the blade-carriers 23.

Thus it can be imagined that, under the action of the spring 58, the active zones 25 of the blades are able to be displaced automatically in the direction of a radial extension vis-a-vis the axis 4, as far as a limit defined by abutment of the lower zones 75 of the arms 24 of the blade-carriers 23, situated below the pivot axes 28 of these latter, against a sleeve 76 connected at its upper end in a removable manner, for instance by screw threads, to the wall 8 in a position radially inside it with respect to the axis 4. The interchangeability of the sleeve 76 permits choice at will of a sleeve determined amongst a range of such sleeves having different dimensional characteristics, as a function of the limit which is wished to be imposed on the radial extension of the active zone 25 of each blade 22 with respect to the axis 4, and mounting of the sleeve 76 thus chosen on the apparatus for offering an appropriate abutment at the zone 75 of each blade carrier 23.

A pivoting of each blade carrier 23 about its axis 28 with respect to the sleeve 29 in a corresponding direction, for the active zone 25 of each blade 27, radially towards the axis 4 can itself be obtained by a manual manoeuvre, thanks to means able to provisionally oppose the action of the spring 58, that is to say reversible.

These means particularly incorporate the rod 32, which has a form generally circularly cylindrical about the axis 77 parallel to the axis 4, and fixes with respect to the support 1 on account of coaxiality, without play, of the rod 32, sleeve 35 and the bore 36 defined above.

Inside the volume 14, the rod 32 has immediately below the face 69 of the flange 37 of the carrier 29 a lower end on which is fixed a crank 78 perpendicular to the axis 77, and which has downwards, in a fixed manner, on an axis 80 parallel to the axis 77 and staggered with respect to the latter, a finger 79 circularly cylindrical about the axis 80 and which is engaged in an upward groove 70 in the collar 62. This groove 70 is particularly delimited by two flanks 71 and 72 parallel to each other and defined by generatrices parallel to the axis 4, which flanks 71 and 72 are mutually separated by a width of the groove 70 substantially equal to the diameter of the finger 79. The groove 70 connects the inner face 63 of the collar 62 to an outer face 73 of this collar also circularly cylindrical about the axis 4 but which delimits the collar 62 radially away from this axis, in a median plane 74 with respect to which the two flanks 71 and 72 of the groove 70 have a curvature such that a rotation of the rod 32 about the axis 77 with respect to the support 1 brings about, on account of the concomitant rotation of the eccentric finger 79 engaged in the groove 70, a rotation of the collar 62 about the axis 4 with respect to the sleeve 50, in one direction or the other as a function of the direction of rotation of the rod 32. The form of the groove 70 is nevertheless such that, if the rod 32 is freed to rotate about the axis 77 with respect to the support 1, the spring 58 automatically brings about a movement of the sleeve 50 upwards, with respect to the carrier 29, driving the collar 62 and with it the rod 32 to rotate about the respective axes 4 and 77 with respect to the support 1 in a direction such that the discs 65 reach the lower zones of the associated parts 61b of the face 61, and a pivoting of the blade-carriers 23 in such a direction that the active zones 25 of the blades 22 are displaced radially away from the axis 4, until the abutment is established between the part 75 of the blade-carriers 23 and the sleeve 76.

The manoeuvring of the rod 32 has then the essential object of bringing the blades back to return their active zones 25 radially towards the axis 4, for defining their starting position for a movement away from this axis, by a manual rotation of this rod 32, about the axis 77, in a direction tending to disengage the discs 65 from the recessed zone 61b of the face 61 of the piece 57, that is to say to withdraw the discs 65, by rolling on the zones 61b, to the zones 61a.

For enabling this limit to be provisionally fixed, and this at will, the rod 32 carries above the wall 12, that is to say outside the volume 14, a manoeuvring button 180 which is fixed in rotation about the axis 77 with respect to the sleeve 35 and the wall 12, and which can itself be immobilised in a temporary manner, and with it the rod 32, against such a rotation.

For this, the button 180 is mounted on the rod 32 relatively slidingly parallel to the axis 77, directly and immediately above the sleeve 35 at the lower part 81 of the button 180, and via a sleeve 82 integrally fixed to the rod 32 at an upper part 83 of the button 180. In this zone, the button 180 carries in a fixed manner a radial pin 84, with reference to the axis which extends through longitudinally elongated apertures 85 in opposite sides of the sleeve 82 and the rod 32 for assuring mutual fixing of the button 180 and the rod 32 in rotation about the axis 77 whilst permitting relative translational, axial, movement parallel to this axis. Further, the lower part 81 of the button 180 has downwards, about the sleeve 35, a plane face 86 which is annular about the axis 77 and perpendicular to it, this plane annular face 86 being provided with a rib 87 oriented radially with respect to the axis 77 and forming a projection downwards, under this face 86. Between this latter and the wall 12 of the support is spaced a collar 88 arranged about the sleeve 35 with a possibility of relative rotation about the axis 77 and relative translation parallel to this axis, this collar 88 presenting downwards a plane annular face 89, perpendicular to the axis 77, in view of its abutment on the wall 12. Upwards, the collar 88 presents a wall 90 also flat, annular and perpendicular to the axis 77 and having a groove 91 oriented radially with respect to the axis 77, which groove has a form complementary to that of the rib 87 of the face 86 of the button 180 for permitting mutual engagement of the button 180 and the collar 88 with mutual unification for rotation about the axis 77. A compression spring 92 is housed in a chamber 93 which the button 180 delimits internally with respect to the rod 32, and on the one hand abuts upwardly against a plane, annular about the axis 77, lower face 94 of the sleeve 82, closing the upper end of the chamber 93, and on the other hand downwardly against a plane, annular about and perpendicular to the axis 77, face 95, directed upwards, which the button 180 has at its lower part 81, about the rod 32. This spring 92 resiliently urges the button 180 downwards tending to maintain the rib 87 and the groove 91 in mutual engagement and the collar 88 in abutment downwards, by its face 89, against the wall 12. On drawing the button 180 upwards, one can nevertheless disengage the rib 87 from the groove 91 and consequently separate the button 180 and the collar 88 for relative rotation about the axis 77. The rib 87 and the aperture 85 are appropriately dimensioned for this.

In order to permit fixing of the button 180, and with it the rod 32 in a determined angular position, with reference to the axis 77. That is to say for fixing the collar 62 in a determined angular position, with reference to the axis 4, and thus defining a position of the sleeve 50 in translational i.e. axial movement with respect to the carrier 29, the collar 88 and the wall 12 have mutual fixing means in relative indexed positions. For example, as is more particularly evident from FIG. 2, the collar 88 carries in a fixed manner a plate 96, having a lower face coplanar with the face 89. This plate 96 has a periphery 97 having a plurality of notches 98 matching a graduation scale 99. These notches 98 are positioned on the same virtual circle centred on the axis 77 and can be engaged, by choice, on a fixed pin 100 which forms an upwards projection, parallel to the axis 4, above the wall 12. The projection formed by this pin 100 is less than the possible axial movement of the button 180 and with it the collar 88, such that on drawing the assembly of the button 180 and the collar 88 upwards, whilst depressing the spring 92, one can disengage from the pin 100 whichever notch 98 is initially engaged on it, and can bring at will another of the notches 98 into alignment with the pin 100 and, on releasing the button 180 and collar 88, permit their descent again towards the support 1 under the action of the spring 92 and in consequence the engagement of the chosen notch 98 on the pin 100. This ensures a new angular fixing of the collar 88 and with it the button 180 and defines a new axial position of the sleeve 50 with respect to the carrier 29.

Thus can be defined, by engagement of different notches 98 on the projection 100, several radial positions of the active zones 25 of the blades 22 which moves radially outward, having movement of the blades in a direction of an extension with respect to this axis 4 under the action of the spring 58. For example, one can thus vary the extent of this radial movement in steps of 0.5 mm, from a value of 3.0 to 5.5. mm, of the distance between the active zones 25 of the blades 22 and the axis 4.

An indexation of the limit of these active zones 25 of the blades 22 towards the axis 4 constitutes one of the adjustments that precede an operation by means of the apparatus. Another adjustment preceding such an operation is that of the slide 44 along the aperture 45, for establishing a limit value of the projection which the active zones 25 of the blades 22 make with respect to the reference surface 3. In addition, preliminary to an operation, the finger 42 can be either brought into a position such that the active zones 25 of the blades 22 are withdrawn with respect to the reference surface 3, or abutted against the slide 44 so that the active zones 25 of the blades form a projection thus predetermined. Then, for marking the optical axis, the support is placed on the eye 2 placing the reference surface 3 in contact with it in such a position that the axis 4 of the support coincides with the optical axis 105, making the penetration of the blades 22 into the cornea if these blades are already projecting. The chamber 9 is then evacuated for assuring fixing of the apparatus on the eye and pressing the cornea against the reference surface, which the cornea fits tightly where covered in the zone 3a. Thereafter, in the case where the active zones 25 of the blades 22 are initially withdrawn, their penetration into the cornea is made, by projection with respect to the reference surface 3, by bringing the finger 42 progressively into abutment against the slide 44. Each incision is thus initially made at the end closest to the axis 4, with a depth determined by the projection which the active zone 25 of each blade 22 forms with respect to the reference surface 3, and more precisely with respect to the zone 3a of this surface. Thereafter, the button 180 is lifted and freed with respect to the collar 88 to allow free turning of this button 180 about the axis 77 and allowed free turning of the collar 62 about the axis 4. The spring 58 is left free to act which brings about an upward movement of the sleeve 50 with respect to the carrier 29 for rolling of the discs 65 on the zones 61b of the face 61 of the piece 59, in a direction corresponding to a descent of the slope of these zones 61b. It should be noted that, for permitting such travel along the zones 61b of the face 61 via the discs 65, which signifies an approach of the piece 57 vis-a-vis the collar 62, it can be judicious to arrange in this latter, apertures such as 101 (FIG. 3), circularly curved about the axis 4, for receiving the zones 61a of the face 61 of the pieces 59 when the discs 65 reach the bottom of the zones 61b of the face 61, which corresponds to a maximum approach of the piece 59 vis-a-vis the collar 62. Upon this movement of the sleeve 50 under the action of the spring 58, the different blade-carriers 23 swing together in a corresponding direction, for the active zones 25 of the different blades 22, to a joint extension vis-a-vis the axis 4, and this movement is continued until the zones 75 of the different blade-carriers 23 come into abutment against the sleeve 76, which defines the limit furthest from the axis 4 of each incision. Between these two limits, the incision has a depth determined by the projection formed by the active zone 25 of the corresponding blade 22 with respect to the zone 3a of the reference surface 3. It should be noted that this projection, and with it the depth of incision, is a function on the one hand of the position given by the carrier 29 by the action on the finger 42, that is to say the adjustment of the slide 44, and on the other hand by the geometry of the zone 3a, which can be advantageously changed by changing the lens 18 which defines it, in a manner to obtain a constant depth of incision or, on the contrary, a depth of incision varying in a pre-determined manner according to the extension vis-a-vis the axis 4. The obtaining of a constant depth of incision is assured if, in each plane 20 including the axis 4, the zone 3a is presented in the form of an arc of a circle centred on the axis 28 perpendicular to this plane 20. An approximation to this form, permitting retention of the same lens 18 for different possible adjustments of the position of the sleeve 29 with respect to the support 1 parallel to the axis 4 is nevertheless admissible. When the incisions are thus terminated, the evacuation in the chamber 9 is interrupted and the active zones of the blades 22 are withdrawn with respect to the reference surface 3, either by detaching the support 1 from the cornea 2, or previous to such a detachment, before dismounting, cleaning and sterilisation of the apparatus.

Naturally, numerous variants can be incorporated into the apparatus which has been described, as to its concrete structure as concerns its geometry.

One of these possible variants is illustrated in FIGS. 4 and 5, where will be found respectively under the references 201 to 226, 228 to 230,232,234 to 237,250,252 to 257,261 to 270,272,273,275 to 296,305,311,341,380 to possible secondary geometric differences close to the elements described above under the references 1 to 26,28 to 30,32,34 to 37,50,52 to 57,61 to 70,72,73,75 to 96,105,111,141,180. The elements corresponding to elements 27,71,74,97 to 101 of the embodiment described with reference to FIGS. 1 to 3 will also be found in the case of the embodiment of FIGS. 4 and 5, but not visible. For the assembly of these common elements, reference should be made to the description on the respective corresponding elements of the embodiment illustrated in FIGS. 1 to 3.

On the contrary, the elements having the references 38 to 49, constituting a part of the means for displacing the carrier 29 axially limiting this translational movement in the case of the embodiment illustrated in FIGS. 1 to 3, as well as the elements 58 to 60 of this embodiment, are replaced by different means in the embodiment of FIGS. 4 and 5.

The compression spring 58, helicoidal about the axis 4, has been replaced by a plurality of helicoidal compression springs 258 housed in the volume 214 and having respective axes parallel to the axis 204, these axes being regularly angularly spaced about this axis 204 and the springs 258 acting, in the same manner as the spring 58, against the shoulder 256 of the wall 211 and the shoulder 257 of the sleeve 250.

The pieces 59 and 60 are in themselves omitted, the sleeve 250 presenting, directly upwards, the annular face 261, having plane zones 261a alternating with sloping recessed zones 261b, in view of rolling of the discs 265 of the collar 262. It should be noted that the face 261 presents in addition, notches 261c in the way of the discs 267 rolling on the collar 262 against the inner face 269 of the flange 237 of the carrier 229. In fact, in this embodiment, the axes 266 and 268 of the discs 265 and 267 are placed coplanar, in the same plane perpendicular to the axis 204, in order to permit a reduction in the congestion of the apparatus in the direction of the axis 204.

In addition, in the embodiment of FIGS. 4 and 5, the guidance of the sleeve 205 in translation with respect to the carrier 229, parallel to the axis 204, is ensured not by sliding against the support 201, as is the case in the example of FIGS. 1 to 3, but by sliding application of an annular bearing 251 of the sleeve 250, which is circularly cylindrical about the axis 204 and directed towards it, against the face 264 of the carrier 229 against which also slides the collar 262.

In themselves, the elements 38 to 49 of the embodiment of FIGS. 1 to 3 are replaced in the following manner.

In the embodiment illustrated in FIGS. 4 and 5, between the upper, annular plane face 238 of the flange 237 of the carrier 229 and a lower, annular plane face 239, which the wall 212 presents to the inside of the volume 214 is arranged an annular, upwards, crown 240, in flat, upwards, contact with the face 239 by the intermediary of a sliding shim 241. Between the outer cylindrical face 230 of the wall 213 and the inner cylindrical 242, of the crown 240 is interposed a ball race 243 which ensures guiding of the crown 240 in rotation. Relative translation of the crown is prevented from the fact that action of the springs 258 elastically urges the sleeve 250 in translation upwards together with, the collar 262 by the intermediary of the discs 266, so that the flange 237 of the carrier 229, via the intermediary of the discs 267, urges the crown 240 upwards via the intermediary of mutual application means. This means having, on the flange 237, a plurality of discs 244 mounted for rotation on this flange about respective radial axes 245 regularly angularly spaced with respect to the axis 204, and under the crown 240 an annular roller track 246 having coplanar zones 246a which are circularly curved about the axis 204 to which they are perpendicular and between which are spaced the recessed sloping zones 246b, for example constituted by helical portions of the same slope about the axis 204. Each of the zones 246b is placed opposite a disc 244 so that the zones 246b and the discs 244 cooperate in the manner of a set of cam followers, respectively, in order that a rotation of the crown 240 in the direction 247 is translated via contact of each disc 244 with the lowest zones of the part 246b of the roller track which constitutes the edge 246, that is to say these zones of which the level is closest to that of the zones 246a, which is translated via a descent of the carrier 229 parallel to the axis 204. It will be noted that, in this example, such a movement is facilitated by the replacement of the annular bearing 31 described with reference to FIGS. 1 to 3 by the ball race 248 interposed between the face 230 of the wall 213 and a circularly cylindrical face 249 directed towards the axis, which face has the flange 237 of the carrier 229.

The slope of the zones 246b constituting the roller track for the discs 244 under the crown 240, as well as the quality of this roller track and the ability to slide of the crown 240 with respect to the wall 212 thanks to the shim 241, are chosen such that there is reversability of movement. That is to say that the urging of the flange 237 upwards by the springs 258 is translated by a rotation of the crown 240 in the direction reverse from the direction 247 axis 204, with respect to the support 201, in the course of which the discs 244 reach the lowest zones, that is to say the greatest heights of their roller track 246b; thus, the springs 258 act in the direction of a withdrawal of the active zones 225 of the blades 222, with respect to the reference surface 203. Moreover, as in the case of the embodiment illustrated in FIGS. 1 to 3, the springs 258 tend to turn the collar 262 about the axis 204 with respect to the carrier 229, in the direction 227 which is opposite to the direction 247, by rolling of each of the discs 265 towards the lowest zones of their roller track 261b, this corresponds to placing the active parts 225 of the blades 222 nearest to the axis 204 if unlocking of the button 280 for manoeuvring the rod 232 is not opposed, as has been said above; it should be noted that, in the example illustrated in FIGS. 4 and 5, the reversability of the transmission of movement between the rod 232 and the collar 262 is ameliorated by a ball race 271 by which the finger 279 enters in contact with the flanks such as 272 of the groove 270 of the collar 262.

For permitting a manoeuvre of the crown 240 in rotation about the axis 204 with respect to the support 201, at will, and a fixing at will against a relative rotation, the crown 240 is pierced, on an axis 274 parallel to the axis 204, by a threaded bore 298 in which is screwed a rod 299 on the axis 274, which traverses the wall 212 via an aperture 300 arranged in it in a circularly curved from about the axis 204; the rod 299 carries about the wall 112 a manoeuvring button 301 which permits screwing or unscrewing of the rod 299 with respect to the bore 298 and thus, respectively, ensuring a fixing of the crown 240 vis-a-vis the wall 212 by screwing of this latter between the crown 240 and the button 301, or on the contrary to free the crown 240 vis-a-vis a rotation with respect to the wall 212, about the axis 204, which permits bringing, by the set of discs 244 and their roller tracks 246b, the carrier 229 into any desired position, in translation parallel to the axis 204, with respect to the support 201 in order to withdraw the active parts 225 of the blades 222 with respect to the reference surface 203, or on the contrary to place them in projection with respect to this latter, at a determined size; advantageously, a graduation similar to the graduation 43 visible in FIG. 2 is carried on the wall 212 for offering a marking of the angular position, with reference to the axis 204, of the crown 240.

It should be noted that the difference in structure of these means of manoeuvring of the sleeve 250 which have been described do not affect at all the functioning of the apparatus, if the description which has been made of this functioning with reference to FIGS. 1 to 3 is compared with that of FIGS. 4 and 5.

Incidentally, it should be noted that the crown 240, of which the radial dimensioning is greater than that permitted by the volume 214, is pierced from time to time, parallel to the axis 204, by a central aperture 302' for permitting passage of the rod 232 and an annular extension of the sleeve 235 from it until it is traversed from the flange 237 via a bore 236 of it.

Other differences which will be described, bringing to the apparatus illustrated in FIGS. 4 and 5 the same possibilities as in the case of the apparatus illustrated in FIGS. 1 to 3, the apparatus illustrated in FIGS. 4 and 5 presents these characteristics offering to it a further possibility. In effect the wall 215 is limited in the direction of height such that it is not necessary to arrange the slot 219, arranged in this case exclusively in the lens 218 and this latter is fixed in a removable manner with the wall 215 by means assuring a fluid tightness, if the assembly formed by the volumes 214 and 216 is delimited in a fluid tight manner by the support 201, and open exclusively towards the reference surface 203, by the slots 219 of the lens 218. This connection 302, comparable in all ways to the connection 311, permits the connection of this volume 214–216 to a source of vacuum, which assists the pressing of the cornea against the lens and reduces the resistance of the cornea to penetration of the blades, thus resulting in a reproducibility of the depth of incision.

For example, to this end, the lens 218 has, in an upper zone, an annular plane shoulder 303, by which it is applied on an annular shoulder 304 which the wall 215 presents in a lower part. The wall 213 has a screw thread 335 permitting screwing of a circularly cylindrical collar 306, having a complementary screw thread 307. Downwards the collar 306 has an annular shoulder 308, which permits application of the lens 218 downwards onto the shoulder 304. The shoulder 308 abuts on the lens via the intermediary of an O-ring 309, about the axis, taking abutment downwards at the same time on the lens and on an immediately adjacent zone of the wall 215. A precise positioning of the lens 218 with respect to the support 201, with reference to the axis 204, is assured by a pin 310 fixed to the lens 218 and forming a projection below the shoulder 303 for penetrating into a complementary notch 321 of the shoulder 304 of the wall 215.

Naturally, a similar mounting can be adopted on the apparatus conforming in other respect to FIGS. 1 to 3.

Similarly, there could be provided on such apparatus, as is illustrated in FIG. 4, a ring 312 housable in the opening 210 of the vacuum chamber 209, without closing it, this ring 312 presenting downwards an indentation 313 for anchoring on the cornea.

Similarly, in the apparatus illustrated in FIGS. 1 to 3 it is possible to adopt the mounting of the blades 222 in the arms 224 of the blade-carriers 223 which is illustrated in FIG. 4 and FIG. 5. That is, a mounting according to which the arm 224, defining as has been described above a blade reception housing 314, carries in a fixed manner two pins traversing this housing 314 from side to side parallel to the axis 228 of pivoting on the carrier 229. In the illustrated example, one 315 of these pins, relatively higher defines also the bearing pin of the blade carriers about the axis 228 on the carrier 229 whilst the other pin 316, relatively lower, is situated close to the lower end of the arm 224. Inside the housing 314 is arranged a blade spring 317 having two notches 318 and 319 for respectively receiving one and the other of the pins 315 and 316, this spring 317 having, when it is viewed in a plane 320 passing through the axis 228 and through the axis 321 of the pin 316, a curvature such that it applies in the immediate area of the notches 318 and 319 of the side of the housing 314, and in a zone intermediate between the two notches 318 and 319 of the other side of the housing 314.

Complementarily, the blade 222 has, in a zone 322, engaged in the housing 314, a slot 324 open opposite from the active part 225 and presenting towards a closed botom, which slot is intended to receive externally the two pins 315 and 316 in application upwards, via its bottom, agains the pin 316. From the curvature of the spring 317, this latter plate part 322 of the side of the housing 314 on which tends to be applied the intermediate zone between the notches 318 and 319, insures a resilient retention of the blade 222 in the arm 224 in such a position that a median plane of the blade 222 includes the axis 204 of the support 201, and coincides with the plane 220 of the associated slot 219.

Such mounting offers security, whilst permitting rapid extraction and insertion of the blade 222 into the blade-carrier 223. Also provided for this is, advantageously, a hole 325 traversing the blade 222 from side to side at the upper part of the active part 225, that is to say immediately close to the part 322 engaged in the arm 224 of the blade-carrier 223.

It will be noted that it is possible to space between the pin 316 and the bottom of the slot 324 a shim for increasing the projection which the active zone 225 of the blade 224 forms under the arm 224 of the associated blade-carrier 223 and, associating these identical blades with such different shims, the simultaneous making of incisions of different depths in view of corrections of myopia with astigmatism. Similarly, it is possible to utilise simultaneously blades of different geometry.

The blades can be of steel, possibly provided with diamond in their active zone, these examples not being limitative.

Naturally, these different variants of the apparatus according to the invention constitute only non-limitative examples, and numerous other variants can be made without departing from the scope of the present invention.

I claim:

1. Radial keratotomy apparatus comprising a support having:
    an axis of the support,
    a concave reference surface secant to the axis of the support and adapted to fit the cornea of an eye in a position in which the axis of the support coincides with the optical axis of the eye,
    a plurality of slots of which each is arranged with a respective plane including the axis of the support and opens into a zone of the reference surface each slot permitting the passage of a blade of such a type that said blade has an active part forming a projection determined with respect to the reference surface and can move in the plane of the slot between two determined limits, respectively of approach and extension of the active part of the blade with respect to the axis of the support,
    characterised in that the support has a plurality of blades of which each is associated with a respective slot, and means, arranged behind the reference surface for bringing about simultaneous displacement of the blades with respect to the support, in the respective associated slots and in their respective planes, from a first of the two said respective determined limits to the second of these two respective determined limits and at the said respective determined projection of an active part of each blade.

2. Apparatus according to claims 1, characterised in that it comprises means for adjusting the position of the said first limit spacedly with respect to the axis of the support.

3. Apparatus according to claims 1, characterised in that it comprises means for adjusting the position of the said second limit spacedly with respect to the axis of the support.

4. Apparatus according to claims 1, characterised in that the said first and second limits are respectively the limit of approach and the limit of extension of the active part of each blade with respect to the axis of the support, the passage of a blade of such a type that said blade has an active part forming a projection determined with respect to the reference surface and can move in the plane of the slot between two determined limits, respectively approaching and extending the active part of the blade with respect to the axis of the support, 5. Apparatus according to claim 1, characterised in that it comprises means for reversible withdrawal of the active part of the blades with respect to the reference surface.

6. Apparatus according to claim 1 characterised in that the blades are removable and interchangeable.

7. Apparatus according to claim 1, characterised in that the reference surface is removable and interchangeable at least as regards an annular zone situated around the axis of the support and into which the slots open.

8. Apparatus according to claim 1, characterised in that the reference surface comprises a face of a lens forming an integral part of the support and having the said slots.

9. Apparatus according to claim 1, characterised in that it comprises means for adjusting the said projection with respect to the reference surface.

10. Apparatus according to claim 1, characterised in that it comprises means for pneumatic pressing of the cornea against the reference surface.

11. Apparatus according to claim 10, characterised in that the support limits in a fluid tight manner, around the blades, a volume open only towards the reference surface particularly via the said slots, and in that it comprises means for connecting the said volume to a source of vacuum.

12. Apparatus according to claim 10, characterised in that the reference surface has a convexity limited to an annular zone situated about the axis of the support and in which the slots open.

13. Radial keratotomy apparaus comprising a support having:
    an axis of the support,
    a concave reference surface secant to the axis of the support and adapted to fit the cornea of an eye in a position in which the axis of the support coincides with the optical axis of the eye,
    a plurality of slots of which each is arranged with a respective plane including the axis of the support and opens into a zone of the reference surface, each slot permitting the passage of a blade of such a type that said blade has an active part forming a projection determined with respect to the reference surface and can move in the plane of the slot between two determined limits, respectively of approach and extension of the active part of the blade with respect to the axis of the support,
    characterised in that it comprises:
    an annular carrier arranged around the axis of the support, and behind the reference surface,
    means for guiding the carrier in translation with respect to the support parallel to the axis of the support,
    means defining two stable, determined limit positions of the carrier with respect to the reference surface of the support on the said translation of the carrier with respect to the support,
    means for manoeuvring at will the carrier in translation with respect to the support between the said limit positions,
    a plurality of blade carriers of which each is associated with a respective slot and pivotally mounted on the carrier about a respective axis perpendicular to the said plane of the associated slot,
    a plurality of blades of which each is fixed to a respective blade carrier, the said blade being arranged in the said plane of the associated slot and having across the associated slot an active part in the region of the reference surface the said active part being withdrawn with respect to the reference surface in a first of said limit positions of the said carrier with respect to the reference surface and forming a projection with respect to the reference surface (3,203) in the second of these two limit positions, means for fixing each of the blades to the associated blade carrier, means defining two stable, determined limit positions of each blade-carrier pivotally with respect to the carrier defining themselves the said two determined limits, respectively of approach and extension of the active part of the blade with respect to the axis of the support, means for manoeuvring at will the assembly of blade-carriers pivotally with respect to the carrier about the said pivot axis, so that the active parts of the blades are moved together from a first of the said limits, respective of approach to and extension from the axis of the support, to the second of these two limits.

14. Apparatus according to claim 13, characterised in that the active part of each blade is arranged in accordance with a plane inclined with a determined angle with respect to the said plane of the associated slot, this angle being identical for all the blades, and in that the guide means for the carrier in translation with respect to the support comprises a mutual connection of the carrier and of the support via a helicoidal cam surface centred on the axis of the support and having a helix angle compatible with the said angle determined so that, during the said translation of the carrier with respect to the support, the said plane of the active part of each blade remains fixed in respect to the support.

15. Apparatus according to claim 13, characterised in that the blades and blade-carriers have mutually disconnectable fixing means.

16. Apparatus according to claim 13, characterised in that the reference surface is removable and interchangeable at least as regards an annular zone situated around the axis of the support and into which the slots open.

17. Apparatus according to claims 13, characterised in that the reference surface comprises a face of a lens forming an integral part of the support and having the said slots.

18. Apparatus according to claim 17 characterised in that the lens is removable.

19. Apparatus according to claim 13, characterised in that the reference face has, internally, a vacuum volume and in that the support has means for connecting the said vacuum volume to a source of vacuum.

20. Apparatus according to claim 19, characterised in that the support limits in a fluid tight manner, around the blades, a volume open only towards the reference surface particularly via the said slots, and in that it comprises means for connecting the said volume to a souce of vacuum.

21. Apparatus according to claim 19 characterised in that the reference surface has a convexity limited to an annular zone situated about the axis of the support and in which the slots open, the said annular zone having a shape approximately corresponding to an envelope of arcs of which each is situated in the said plane of a respective slot and centred on the pivot axis of the blade-carrier associated with respect to the carrier.

22. Apparatus according to claim 13, characterised in that the active part of each blade is arranged in accordance with the said plane of the associated slot, and in that the guide means for the carrier in translation with respect to the support have means preventing any rotation of the carrier with respect to the support about the axis of the support.

23. Apparatus according to claim 21, characterised in that the means for manoeuvring the carrier in translation with respect to the support comprises a crown carried by the support with the possibility of relative rotation about the axis of the support without possibility of relative translation parallel to the axis, mutually engaged screw threads, arranged respectively on the carrier and on the said crown, and means for manoeuvring at will the said crown in rotation with respect to the support, about the axis of the support.

24. Apparatus according to claim 21, characterised in that the means for manoeuvring the carrier in translation with respect to the support comprise a crown carried by the support with the possibility of relative rotation about the axis of the support without possibility of relative translation parallel to this axis, the said crown and the carrier being in mutual engagement via the intermediary of at least one cam track carried by one of them and sloped with reference to the axis of the support and at least one cam follower carried by the other between them opposite the cam track, means for ensuring a mutual contact of the cam follower and of the cam track, means for manoeuvring at will the said crown in rotation with respect to the support, about the axis of the support.

25. Apparatus according to claim 23 or claim 24, characterised in that means defining two stable limit positions of the carrier with respect to the reference surface of the support comprise abutment means for imposing on the rotation of the crown with respect to the support, about the axisof the support, limits of rotation corresponding to the said first and second limit positions of the carrier with respect to the reference surface.

26. Apparatus according to claims 13, characterised in that it comprises means for adjusting the said second limit position of the carrier with respect to the reference surface.

27. Apparatus according to claim 25 characterised in that it comprises means for adjusting at least the one of the limits of rotation of the crown with respect to the support which corresponds to the second limit position of the carrier with respect to the reference surface.

28. Apparatus according to claim 13, characterised in that it comprises means for adjusting the position of the said first limit spacedly with respect to the axis of the support.

29. Apparatus according to claim 13, characterised in that it comprises means for adjusting the position of the said second limit spacedly with respect to the axis of the support.

30. Apparatus according to claim 13, characterised in that the means for manoeuvring the assembly of blade-carriers pivotally with respect to the carrier comprise:

an annular sleeve coaxial with the carrier, means for guiding the sleeve in translation with respect to the carrier parallel to the axis of the support without possibility of relative rotation about the axis of the support, means for kinematic connection between the sleeve and each of the blade-carriers, associatng with a translation of the sleeve with respect to the carrier in one or other of two opposite directions parallel to the axis of the support a simultaneous pivoting of the assembly of blade-carriers with respect to the carrier so that the active parts of the blades are displaced respectively towards or away from the axis of the support, means for manoeuvring at will the sleeve in translation with respect to the carrier in one or other of the said two opposite directions.

31. Apparatus according to claim 30, characterised in that the said means of kinematic connection between the sleeve and each of the blade-carriers associate to a translation of the sleeve in the first of the said two opposite directions with respect to the carrier, a simultaneous pivoting of the assembly of the blade-carriers with respect to the carrier such that the active parts of the blades are displaced from the said limit of approach with respect to the axis of the support, constituting the same first limit, to the said limit of extension with respect to the axis of the support, constituting the said second limit.

32. Apparatus according to claim 30, characterised in that the means for manoeuvring the sleeve in translation with respect to the carrier comprises:

means for resiliently urging the sleeve in translation in a first of said two opposite directions with respect to the carrier, reversible means for manoeuvring the sleeve in translation with respect to the carrier in the second of the said two opposite directions, means for temporarily fixing the sleeve against a translation under the action of the resilient urging means with respect to the carrier, for defining the said first of the said limits respectively of approach and of extension of the active parts of the blades with respect to the axis of the support, means for defining the said second of the said limits respectively of approach and of extension of the active parts of the blades with respect to the axis of the support.

33. Apparatus according to claim 32, characterised in that the reversible means for manoeuvring the sleeve in translation with respect to the carrier in the said second direction comprise a collar carried by the carrier with possibility of relative rotation about the axis of the support without possibility of relative translation parallel to the axis; the said collar and the sleeve being in mutual engagement by the intermediary of at least one cam track carried by one of them and sloping with reference to the axis of the support and at least one cam follower carried by the other between them opposite the cam track, means for assuring a mutual contact of the cam follower and of the cam track, and means for manoeuvring at will the said collar in rotation with respect to the carrier, about the axis of the support, and in that means of provisional fixing of the sleeve against a translation under the action of resilient urging means comprising means for provisional fixing of the said collar against a rotation with respect to the carrier about the axis of the support.

34. Apparatus according to claim 33, characterised in that the means for provisionally fixing the said collar against a rotation with respect to the carrier about the axis of the support comprise indexation means with a plurality of relative angular positions of provisionally fixing of the said collar with respect to the carrier, with respect to the axis of the support.

35. Apparatus according to claim 32, characterised in that the means for defining the said second of the said limits comprise an annular abutment, fixed to the support, for the blade-carriers.

36. Apparatus according to claim 35, characterised in that the said annular abutment and the support have means for mutual adjustable fixing.

* * * * *